(12) United States Patent
Fotouhi et al.

(10) Patent No.: US 6,313,143 B1
(45) Date of Patent: Nov. 6, 2001

(54) SUBSTITUTED PYRROLES

(75) Inventors: Nader Fotouhi, Chatham; Emily Aijun Liu, Nutley; Allen John Lovey, North Caldwell; John Guilfoyle Mullin, Jr., Hawthorne; Giuseppe Federico Weber, Cedar Grove, all of NJ (US)

(73) Assignee: Hoffmann-La Roche Inc., Nutley, NJ (US)

( * ) Notice: Subject to any disclaimer, the term of this patent is extended or adjusted under 35 U.S.C. 154(b) by 0 days.

(21) Appl. No.: 09/707,678

(22) Filed: Nov. 7, 2000

Related U.S. Application Data
(60) Provisional application No. 60/171,051, filed on Dec. 16, 1999.

(51) Int. Cl.[7] .................... A61P 35/00; C07D 403/04
(52) U.S. Cl. .................. 514/323; 514/414; 548/414; 548/455; 548/111; 546/201
(58) Field of Search ................... 514/414, 323; 548/414, 455, 111; 546/201

(56) References Cited

U.S. PATENT DOCUMENTS

| | | | |
|---|---|---|---|
| 5,057,614 | 10/1991 | Davis et al. | 548/466 |
| 5,856,517 | 1/1999 | Huryn et al. | 548/455 |
| 5,891,901 | * 4/1999 | Dhingra et al. | 514/414 |
| 6,030,994 | 2/2000 | Huryn et al. | 514/414 |
| 6,048,887 | 4/2000 | Dhingra et al. | 514/414 |

FOREIGN PATENT DOCUMENTS

| | | |
|---|---|---|
| WO-96/04906 | * 2/1996 | (WO) . |
| WO 98/04551 | 2/1998 | (WO) . |
| WO-99/47518 | * 9/1999 | (WO) . |

OTHER PUBLICATIONS

Davis, P. D. et al., Inhibitors of Protein Kinase C. 1.[1] 2,3–Bisarylmaleimides, Journal of Medicinal Chemistry, US, American Chemical Society, Washington, vol. 35, No. 1, 1992 pp. 177–184.

* cited by examiner

*Primary Examiner*—Robert W. Ramsuer
*Assistant Examiner*—Golam M. M. Shameem
(74) *Attorney, Agent, or Firm*—George W. Johnston; Patricia S. Rocha-Tramaloni

(57) ABSTRACT

Disclosed are novel substituted pyrroles having the formula

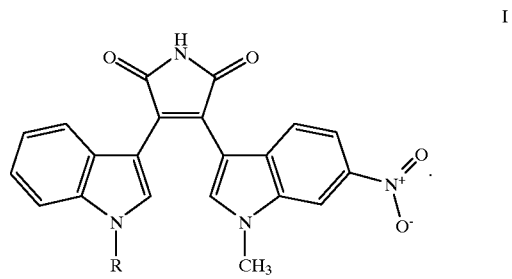

These compounds and their pharmaceutically acceptable salts are suitable for administration to patients as continuous infusion solution and are useful in the treatment and/or control of cell proliferative disorders, in particular cancer. Also disclosed are pharmaceutical compositions containing the foregoing compounds and methods for the treatment and/or control of cancer.

17 Claims, No Drawings

SUBSTITUTED PYRROLES

This application claims priority under 35 U.S.C. §119(e) of provisional application(s) Serial No. 60/171,051 filed on Dec. 16, 1999.

BRIEF SUMMARY OF THE INVENTION

The present invention is directed to certain substituted pyrroles that are antiproliferative agents. These compounds and their pharmaceutically acceptable salts are useful in the treatment or control of cell proliferative disorders, in particular cancer. The invention is also directed to pharmaceutical compositions containing such compounds, and to methods for the treatment and/or prevention of cancer, particularly the treatment or control of solid tumors.

BACKGROUND OF THE INVENTION

Uncontrolled cell proliferation is the hallmark of cancer. Cancerous tumor cells typically have some form of damage to the genes that directly or indirectly regulate the cell-division cycle. Much research has been expended in the study of antiproliferative agents. While many agents have been identified having desired antiproliferative activities, many of these agents have various drawbacks, including poor solubility, molecular complexity, etc., which may render them either unsuitable or inconvenient for therapeutic use in human patients. There continues to be a need for small molecule compounds that may be readily synthesized, are effective as cancer therapeutic agents and are suitable for continuous infusion delivery to patients. It is thus an object of this invention to provide such compounds as well as pharmaceutical compositions containing such compounds.

Definitions

As used herein, the following terms shall have the following definitions.

"Alkenyl" means a straight-chain or branched aliphatic unsaturated hydrocarbon having 1 to 15 carbon atoms, preferably 1 to 10 carbon atoms, most preferably 1 to 6 carbon atoms.

"Alkoxy" means an alkyl or alkenyl group that is attached to the remainder of the molecule by oxygen (e.g. RO—, such as methoxy, ethoxy, etc.).

"Aryl" means an aromatic ring having 5 to 10 atoms and consisting of 1 or 2 rings, which optionally may include one or more heteroatoms that are the same or different. For the purposes of this definition, aryl includes heteroaryl. Preferred heteroatoms include nitrogen, sulfur, or oxygen, singly or in any combination, in place of one or more of the carbons. Examples of aryl groups within this definition are phenyl, pyridine, imidazole, pyrrole, triazole, furan, pyrimidine.

"Cycloalkyl" means a non-aromatic, partially or completely saturated cyclic aliphatic hydrocarbon group containing 3 to 8 atoms. Examples of cycloalkyl groups include cyclopropyl, cyclopentyl and cyclohexyl.

"Effective amount" means an amount of at least one compound of Formula I or a pharmaceutically acceptable salt thereof that significantly inhibits proliferation and/or prevents differentiation of a human tumor cell, including human tumor cell lines.

"Hetero atom" means an atom selected from nitrogen, sulfur and oxygen. Hetero atoms are independently selected and may replace one or more carbon atoms.

"Heterocycle" means a 3- to 10- membered non-aromatic, partially or completely saturated hydrocarbon group that contains at least one hetero atom. Such ring systems include, morpholine, pyrrolidine, piperidine, piperazine "$IC_{50}$" refers to the concentration of a particular compound according to the invention required to inhibit 50% of a specific measured activity. $IC_{50}$ can be measured, inter alia, as is described in Example 15, infra.

"Lower alkyl" denotes a straight-chain or branched saturated aliphatic hydrocarbon having 1 to 6, preferably 1 to 4, carbon atoms. Lower alkyl groups may be substituted as specifically provided infra. In addition the alkyl chain may include one or more hetero atoms in lieu of one or more carbon atoms. Typical lower alkyl groups include methyl, ethyl, propyl, isopropyl, butyl, t-butyl, 2-butyl, pentyl, hexyl, and the like.

"Pharmaceutically acceptable salt" refers to conventional acid-addition salts or base-addition salts that retain the biological effectiveness and properties of the compounds of formula I and are formed from suitable non-toxic organic or inorganic acids or organic or inorganic bases. Sample acid-addition salts include those derived from inorganic acids such as hydrochloric acid, hydrobromic acid, hydroiodic acid, sulfuric acid, phosphoric acid and nitric acid, and those derived from organic acids such as acetic acid, tartaric acid, salicylic acid, methanesulfonic acid, succinic acid, citric acid, malic acid, lactic acid, fumaric acid, and the like. Sample base-addition salts include those derived from ammonium, potassium, sodium and, quaternary ammonium hydroxides, such as for example, tetramethylammonium hydroxide.

"Pharmaceutically acceptable," such as pharmaceutically acceptable carrier, excipient, etc., means pharmacologically acceptable and substantially non-toxic to the subject to which the particular compound is administered.

"Pharmaceutically active metabolite" means a metabolic product of a compound of formula I which is pharmaceutically acceptable and effective.

"Polyethylene glycol" or "PEG" groups represent structures of the general formula $^-R^9(OCH_2CH_2)_nOH$, where n is on average between 2 and 1500, preferably 15 to 150, with an average molecular weight of 500 to 5000 Daltons, and wherein $R^9$ is carboxy or lower alkyl, preferably methyl or ethyl.

"Prodrug" refers to a compound that may be converted under physiological conditions or by solvolysis to a pharmaceutical active compound. A prodrug may be inactive when administered to a subject but is converted in vivo to an active compound.

"Substituted," as in substituted alkyl, means that the substitution can occur at one or more positions and, unless otherwise indicated, that the substituents at each substitution site are independently selected from the specified options.

"Substituted amino" means an amino group, which is mono- or di-substituted with another group, preferably lower alkyl (e.g. methyl, or ethyl).

DETAILED DESCRIPTION OF THE INVENTION

Specifically, the invention relates to substituted pyrroles having the formula:

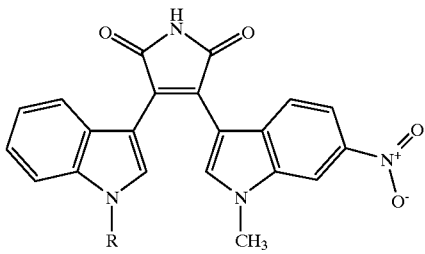

I and pharmaceutically acceptable salts of the foregoing compounds, wherein:

R is selected from the group consisting of —$PO_3R^1R^2$, —$CHR^3OCOR^4$, —$CHR^3OCO_2R^4$, —$CHR^3OCONHR^4$ and —$COR^4$;

$R^1$ and $R^2$ are selected from the group consisting of H, Na and $NH_4$, and are the same unless either $R^1$ or $R^2$ is H, in which case the other can be different, or alternatively, $R^1$ and $R^2$ together represent Ca;

$R^3$ is selected from the group consisting of H or methyl;

$R^4$ is selected from a group consisting of lower alkyl, which may be optionally substituted by one or more substituents selected from the group consisting of —$CO_2R^5$, —$NR^6R^7$, polyethylene glycol, —$OPO_3R^1R^2$, hydroxy, alkoxy, and aryl, alkenyl, which may be optionally substituted by one or more substituents selected from the group consisting of —$CO_2R^5$, —$NR^6R^7$, polyethylene glycol, —$OPO_3R^1R^2$, hydroxy, alkoxy, and aryl, cycloalkyl, which may be optionally substituted by one or more substituents selected from the group consisting of —$CO_2R^5$, —$NR^6R^7$, polyethylene glycol, —$OPO_3R^1R^2$, hydroxy, alkoxy, and aryl.

heterocycle, which when including N as a hetero atom the N optionally may be substituted with —$COR^8$, and aryl which optionally may be substituted by one or more substituents selected from the group consisting of —$CO_2R^5$, hydroxy, alkoxy, polyethylene glycol, —$OPO_3R^1R^2$, and lower alkyl which itself may be substituted with hydroxy, carboxy, and substituted amino;

$R^5$ is selected from the group consisting of H, Na, or lower alkyl;

$R^6$ and $R^7$ are each independently selected from H, lower alkyl, and —$COR^8$, or alternatively, the group —$NR^6F^7$ forms a 5 or 6 membered heterocyclic ring; and $R^8$ is lower alkyl, which optionally may be substituted with a polyethylene glycol.

The compounds of this invention have antiproliferative activity, specifically, they inhibit cell division in G2/M phase of the cell cycle and are generally referred to as "G2/M phase cell-cycle" inhibitors. These compounds are soluble prodrugs of an active metabolite of an anticancer therapeutic agent within U.S. Pat. No. 5,057,614 (Davis et al.), and are thus suitable for continuous infusion delivery.

The present invention is further directed to pharmaceutical compositions comprising a pharmaceutically effective amount of any one or more of the above-described compounds and a pharmaceutically acceptable carrier or excipient.

The present invention is also directed to a method for treating solid tumors, in particular breast or colon tumors, by administering to a human patient in need of such therapy an effective amount of a compound of formula I and/or its pharmaceutically acceptable salts.

In a preferred embodiment of the compounds of formula 1, R is —$CHR^3OCOR^4$. Most preferably $R^3$ is H and $R^4$ is lower alkyl that is substituted with polyethylene glycol.

In another preferred embodiment of the compounds of formula I, R is —$COR^4$. More preferably, $R^4$ is selected from the group consisting of heterocycle and lower alkyl, most preferably lower alkyl that is substituted with —$NR^6R^7$.

In another preferred embodiment of the compounds of formula I, the polyethylene glycol has a molecular weight of from about 750 to about 5000 Daltons, most preferably about 2000 Daltons.

The following are examples of preferred compounds of formula I:

3-[2-(2-Methoxy-ethoxy)-ethoxy]-propionic acid 3-[4-(1-methyl-6-nitro-1 H-indol-3-yl)-2,5-dioxo-2,5-dihydro-1H-pyrrol-3-yl]-indol-1-ylmethyl ester;

O-[2-[[2,5-dihydro-3-[4-(1-methyl-6-nitro-1H-indol-3-yl)-2,5-dioxo-2,5-dihydro-pyrrol-3-yl]-indol-1-yl]methoxycarbonyl]ethyl]-O'-methylpolyethylene glycol 2000;

2,3-Dimethoxy-benzoic acid 3-[4-(1-methyl-6-nitro-1H-indol-3-yl)-2,5-dioxo-2,5-dihydro-1H-pyrrol-3-yl]-indol-1-ylmethyl ester;

3-Diethylaminomethyl-benzoic acid 3-[4-(1-methyl-6-nitro-1H-indol-3-yl)-2,5-dioxo-2,5-dihydro-1H-pyrrol-3-yl]-indol-1-ylmethyl ester hydrochloride;

3-(1H-Indol-3-yl)-4-(1-methyl-6-nitro-1H-indol-3-yl)-1-octadec-9-enoyl-pyrrol-2,5-dione;

{3-[4-(1-Methyl-6-nitro-1H-indol-3-yl)-2,5-dioxo-2,5-dihydro-1H-pyrrol-3yl]-indol-1-yl}-phosphonic acid;

3-(1-Acetyl-1H-indol-3-yl)-4-(1-methyl-6-nitro-1H-indol-3-yl)-pyrrole-2,5-dione;

Trifluoro-acetic acid 3-(1-methyl-6-nitro-1H-indol-3-yl)-4-[1-(piperidine-4-carbonyl)-1H-indol-3-yl]-pyrrole-2,5-dione;

3-(1-Aminoacetyl-1H-indol-3-yl)-4-(1-methyl-6-nitro-1H-indol-3-yl)-pyrrole-2,5-dione hydrochloride;

Acetic acid 3-[4-(1-methyl-6-nitro-1H-indol-3-yl)-2,5-dioxo-2,5-dihydro-1H-pyrrol-3-yl]-indol-1-ylmethyl ester;

Pentanedioic acid mono-{3-[4-(1-methyl-6-nitro-1H-indol-3-yl)-2,5-dioxo-2,5-dihydro-1H-pyrrol-3-yl]-indol-1-ylmethyl} ester;

2,3-Dimethoxy-benzoic acid 1-{3-[4-(1-methyl-6-nitro-1H-indol-3-yl)-2,5-dioxo-2,5-dihydro-1H-pyrrol-3-yl]-indol-1-yl}-ethyl ester; and 3-Diethylaminomethyl-benzoic acid 1-{3-[4-(1-methyl-6-nitro-1H-indol-3-yl)-2,5-dioxo-2,5-dihydro-1H-pyrrol-3-yl]-indol-1-yl}-ethyl ester hydrochloride.

The compounds disclosed herein and covered by the above formulae may exhibit tautomerism or structural isomerism. It is intended that the invention encompasses any tautomeric or structural isomeric form of these compounds, or mixtures of such forms, and is not limited to any one tautomeric or structural isomeric form utilized within the formulae drawn above.

Synthesis of Compounds According to the Invention

The compounds of the invention may be prepared by processes known in the art. Suitable processes for synthesizing these compounds are provided in the examples. Generally, these compounds may be prepared according to the following synthesis schemes.

Compounds of formula I, in which R signifies —PO$_3$R$^1$R$^2$, and in which R$^1$ and R$^2$ are as described above, may be prepared as indicated in scheme I below.

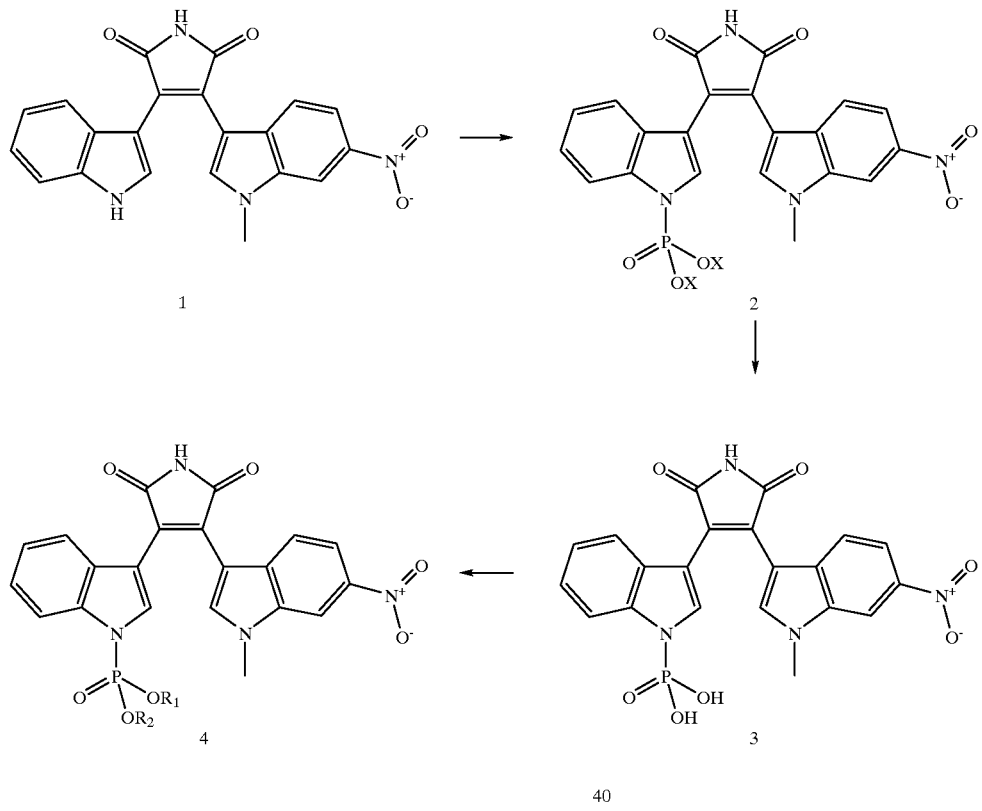

As indicated in scheme I, 3-(1H-indol-3-yl)-4-(1-methyl-6-nitro-1H-indol-3-yl)-pyrrole-2,5-dione (1), (prepared as described in copending U.S. Ser. No. 09/268,887, the relevant portions of which are herein incorporated by reference), was treated with a suitably protected chlorophosphonate in the presence of a strong base, such as lithium bis(trimethylsilyl)amide, in an appropriate solvent such as THF, to afford the protected phosphonic acid derivative 2, in which X represents a suitable protecting group known to those skilled in the art, such as benzyl. Removal of the protecting groups may be achieved by any of the standard methods known to those skilled in the art to give the phosphonic acid 3. In particular, when X represents a benzyl group, the protective groups are removed by using cyclohexadiene and palladium on carbon as a catalyst. Compound 3 can then be converted to its salt 4, such as a monosodium salt, by standard methods also known to those skilled in the art.

Compounds of formula 1, in which R signifies —COR4, may be prepared according to scheme II below.

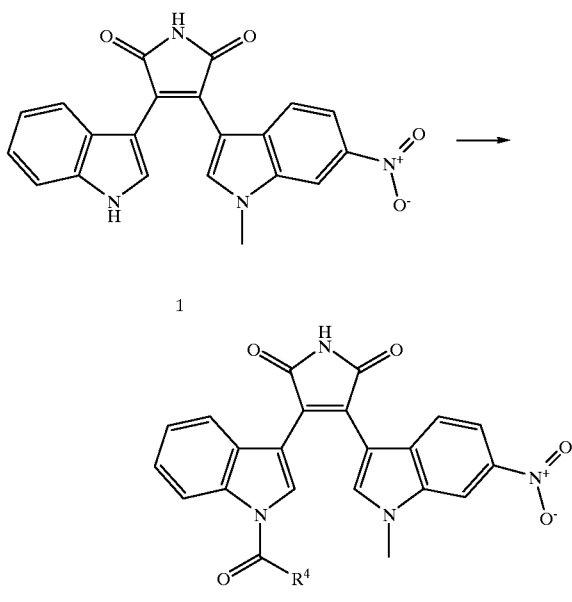

Typically, 3-(1H-indol-3-yl)-4-(1-methyl-6-nitro-1H-indol-3-yl)-pyrrole-2,5-dione (compound 1, prepared as described above in Scheme I) is deprotonated in a aprotic solvent such as THF at −60° C. using a strong base such as lithium bis(trimethylsilyl)amide. The resulting anion is then treated with a known acid chloride or an acid chloride prepared by known methods. Alternatively, compound 1 may be coupled to a known carboxylic acid, or a carboxylic acid prepared by known methods, using standard amide bond formation procedures, such as diisopropylcarbodiimide and HOBt. Compound 5 wherein $R^4$ contains a suitably protected carboxyl, hydroxyalkyl, amino or monoalkylamino, may be further modified by removing the protective group by known methods, and then optionally modifying the resulting carboxyl, hydroxy, or amino group to the desired amide or ester by methods known to those skilled in the art.

Compounds of the general formula I in which R signifies —$CHR^3OCOR^4$, can be prepared according to scheme III below.

Scheme III

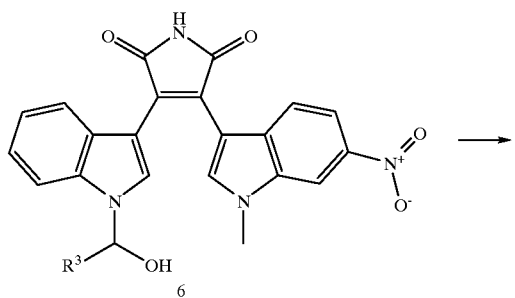

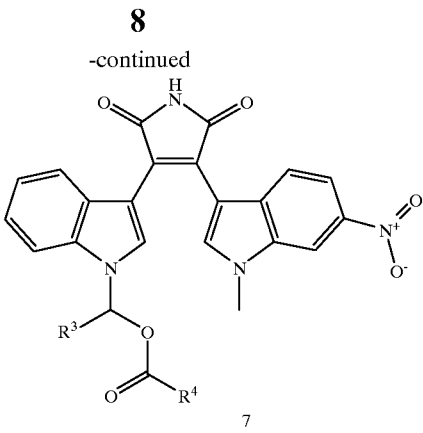

As indicated in Scheme III above, the hydroxy alkyl derivative 6 is esterified using known procedures. Typically, compound 6 is treated with a known carboxylic acid or a carboxylic acid prepared by known methods, in a solvent such as methylene chloride in the presence of EDC and dimethylaminopyridine for several hours at room temperature. Alternatively, the hydroxy intermediate 6 may be treated with a known acid chloride or an acid chloride prepared from known methods. Alternatively, the hydroxy intermediate 6 may be treated with a known acid anhydride or an acid anhydride prepared from known methods.

To prepare compound 7 wherein $R^4$ contains a heteroaromatic ring, the heteroatom, such as N, may be further modified by reaction with an alkyl iodide, such as —$CH_3I$, in a solvent such as acetonitrile.

Alternatively compound 7 where in $R^4$ contains a suitably protected carboxyl, hydroxyalkyl, amino or monoalkylamino, may be further modified by removing the protecting group by known methods, and then optionally modifying the resulting carboxyl, hydroxy, or amino group to the desired amide or ester by methods known to those skilled in the art.

The starting material 6 wherein $R^3$ signifies H, can be prepared also as described in U.S. patent application Ser. No. 09/268,887 (Compound II), the relevant portions of which are herein incorporated by reference.

Starting material 6 wherein $R^3$ signifies methyl may be prepared pursuant to Scheme IV below.

Scheme IV

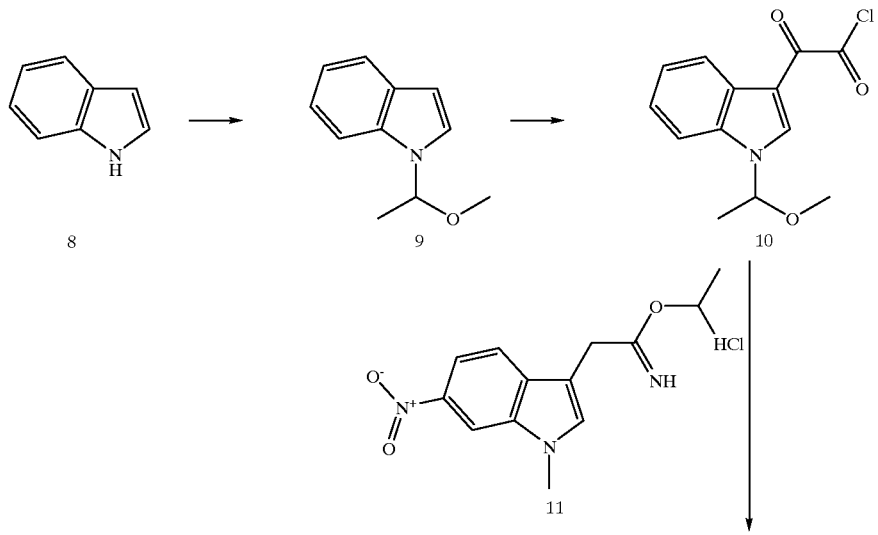

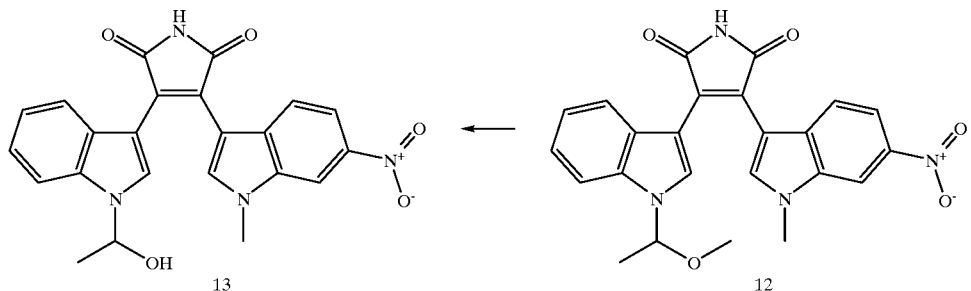

Compound 8 is commercially available (for example from Aldrich).

Compounds of the general formula I in which R signifies —CHR³OCO₂R⁴, and in which R³ and R⁴ are as described above, may be prepared pursuant to scheme V below.

Scheme V

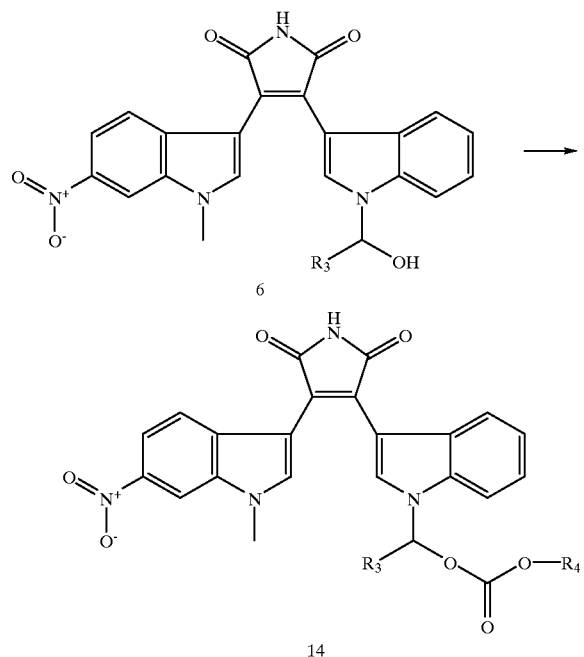

Typically, the hydroxy alkyl derivative 6 is treated with a known chloroformate or a chloroformate prepared using known procedures, in a solvent such as dichloromethane at temperatures of −78 to 20, in the presence of dimethylaminopyridine to afford the desired carbonate 14.

Compounds of the general formula I in which R signifies —CHR³OCONHR⁴, and in which R³ and R⁴ are as described above, may be prepared according to scheme VI below.

Scheme VI

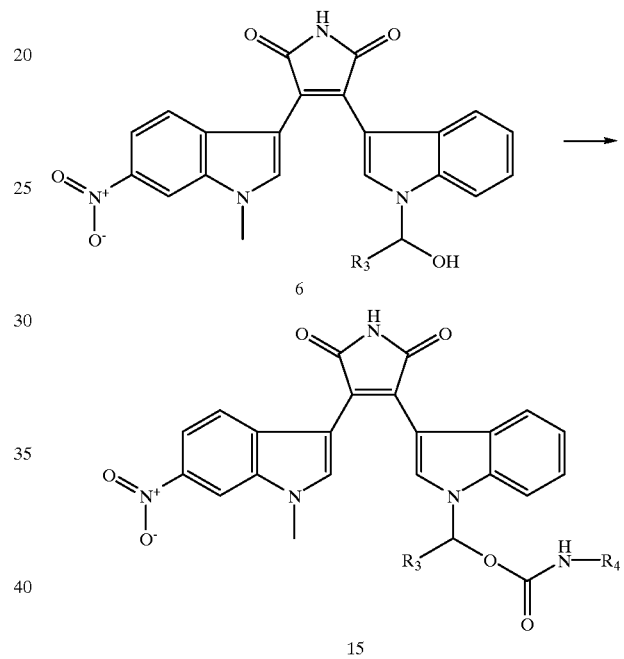

Typically, hydroxymethyl intermediate 6 is deprotonated using a strong base such as lithium bis(trimethylsilyl)amide in a solvent such as THF at 0° C. The anion generated is then treated in the same solvent with bis(p-nitrophenyl) carbonate, followed by a known amine or an amine prepared using known procedures.

Acidic compounds of formula I may be converted into a pharmaceutically acceptable salt by treatment with a suitable base by processes known to those skilled in the art. Suitable salts are those derived not only from inorganic bases, for example, sodium, potassium or calcium salts, but also from organic bases such as ethylenediamine, monoethanolamine or diethanolamine. The conversion of a basic compound of formula I into a pharmaceutically acceptable salt can be carried out by treatment with a suitable acid in a known manner. Suitable salts are those derived not only from inorganic acids, for example, hydrochlorides, hydrobromides, phosphates or sulphates, but also from organic acids, for example, acetates, citrates, fumarates, tartrates, maleates, methanesulphonates or p-toluenesulphonates.

Compositions/Formulations

In an alternative embodiment, the present invention is directed to pharmaceutical compositions comprising at least one compound of formula I or a pharmaceutically acceptable salt thereof.

These pharmaceutical compositions can be administered orally, for example, in the form of tablets, coated tablets, dragees, hard or soft gelatin capsules, solutions, emulsions or suspensions. They can also be administered rectally, for example, in the form of suppositories. In particular, however, the compounds of the present invention are suitable for parenteral administration, for example, in the form of injection solutions.

The pharmaceutical compositions of the present invention comprising compounds of formula I, prodrugs of such compounds, or the salts thereof, may be manufactured in a manner that is known in the art, e.g. by means of conventional mixing, encapsulating, dissolving, granulating, emulsifying, entrapping, dragee-making, or lyophilizing processes. These pharmaceutical preparations can be formulated with therapeutically inert, inorganic or organic carriers. Lactose, corn starch or derivatives thereof, talc, steric acid or its salts can be used as such carriers for tablets, coated tablets, dragees and hard gelatin capsules. Suitable carriers for soft gelatin capsules include vegetable oils, waxes and fats. Depending on the nature of the active substance, no carriers are generally required in the case of soft gelatin capsules. Suitable carriers for the manufacture of solutions and syrups are water, polyols, saccharose, invert sugar and glucose. Suitable carriers for injection are water, alcohols, polyols, glycerine, vegetable oils, phospholipids and surfactants. Suitable carriers for suppositories are natural or hardened oils, waxes, fats and semi-liquid polyols.

The pharmaceutical preparations can also contain preserving agents, solubilizing agents, stabilizing agents, wetting agents, emulsifying agents, sweetening agents, coloring agents, flavoring agents, salts for varying the osmotic pressure, buffers, coating agents or antioxidants. They can also contain other therapeutically valuable substances, including additional active ingredients other than those of formula I.

Dosages

As mentioned above, the compounds of the present invention are useful in the treatment or control of cell proliferative disorders, in particular oncological disorders. These compounds and formulations containing said compounds are particularly useful in the treatment or control of solid tumors, such as, for example, breast and colon tumors.

A therapeutically effective amount of a compound in accordance with this invention means an amount of compound that is effective to prevent, alleviate or ameliorate symptoms of disease or prolong the survival of the subject being treated. Determination of a therapeutically effective amount is within the skill in the art.

The therapeutically effective amount or dosage of a compound according to this invention can vary within wide limits and will be adjusted to the individual requirements in each particular case. In general, in the case of oral or parenteral administration to adult humans weighing approximately 70 Kg, a daily dosage of about 10 mg to about 10,000 mg, preferably from about 200 mg to about 1,000 mg, should be appropriate, although the upper limit may be exceeded when indicated. The daily dosage can be administered as a single dose or in divided doses, or for parenteral administration, it may be given as continuous infusion.

EXAMPLES

The compounds of the present invention may be synthesized according to known techniques, such as, for example, the general schemes provided above. The following examples illustrate preferred methods for synthesizing the compounds and formulations of the present invention.

Example 1

3-[2-(2-Methoxy-ethoxy)-ethoxy]-propionic acid 3-[4-(1-methyl-6-nitro-1H-indol-3-yl)-2,5-dioxo-2,5-dihydro-1H-pyrrol-3-yl]-indol-1-ylmethyl ester A suspension of 1-ethyl-3-(3-dimethylaminopropyl) carbodiimide.HCl ("EDC.HCL"; Aldrich, 77 mg, 0.40 mmol) in dry THF (12 ml) was treated with DMAP (Aldrich) (55 mg, 0.45 mmol) for 2 min at 22° C. To this was added 3-(1-hydroxymethyl-1H-indol-3-yl)-4-(1-methyl-6-nitro-1H-indol-3-yl)-pyrrole-2,5-dione(110 mg, 0.26 mmol) (prepared below). The mixture was stirred for 20 min and to this was added 2-(2-methoxy-ethoxy)-ethoxy]-propionic acid (CAS: 209542-49-4) (120 mg, 0.62 mmol). Stirring was continued at 22° C. for 4 hr. All solvent was evaporated and the product was purified by silica gel chromatography to give 130 mg of 3-[2-(2-methoxy-ethoxy)-ethoxy]-propionic acid 3-[4-(1-methyl-6-nitro-1H-indol-3-yl)-2,5-dioxo-2,5-dihydro-1H-pyrrol-3-yl]-indol-1-ylmethyl ester. (Yield 80 %) 3-(1-hydroxymethyl-1H-indol-3-yl)-4-(1-methyl-6-nitro-1H-indol-3-yl)-pyrrole-2,5-dione was prepared as described in U.S. Ser. No. 09/268,887 (Compound II), the relevant portions of which are herein incorporated by reference.

Example 2

O-[2-[[2,5-dihydro-3-[4-(1-methyl-6-nitro-1H-indol-3-yl)-2,5-dioxo-2,5-dihydro-pyrrol-3-yl]-indol-1-yl]methoxycarbonyl]ethyl]-O'-methylpolyethylene glycol 2000

To a solution of 3-(1-hydroxymethyl-1H-indol-3-yl)-4-(1-methyl-6-nitro-1H-indol-3-yl) pyrrole-2,5-dione (200 mg, 0.5 mmol) (prepared as described above in Example 1) in dichloromethane was added at −78° C., triethylamine (0.6 mmol) followed by O-(2-carboxyethyl)-O'-methyl polyethylene glycol 2000 acid chloride (0.6 mmol) (prepared by standard methods from mono-methyl polyethylene glycol 2000 propanoic acid). The solution was stirred at room temperature for 3 hours, and the solvent was evaporated. The residue was purified by silica gel flash chromatography to yield 1 gm of O-[2-[[2,5-dihydro-3-[4-(1-methyl-6-nitro-1H-indol-3-yl)-2,5-dioxo-2,5-dihydro-pyrrol-3-yl]-indol-1-yl]methoxycarbonyl]ethyl]-O'-methylpolyethylene glycol 2000. (Yield 80%).

Example 3

Using the same procedure as in example 2 the following compounds were prepared:

a) 2,3-Dimethoxy-benzoic acid 3-[4-(1-methyl-6-nitro-1H-indol-3-yl)-2,5-dioxo-2,5-dihydro-1H-pyrrol-3-yl]-indol-1-ylmethyl ester;

b) 3-Diethylaminomethyl-benzoic acid 3-[4-(1-methyl-6-nitro-1H-indol-3-yl)-2,5-dioxo-2,5-dihydro-1H-pyrrol-3-yl]-indol-1-ylmethyl ester hydrochloride.

Example 4

3-(1H-Indol-3-yl)-4-(1-methyl-6-nitro-1H-indol-3-yl)-1-octadec-9-enoyl-pyrrole-2,5-dione A solution of 3-(1H-indol-3-yl)-4-(1-methyl-6-nitro-1H-indol-3-yl)-pyrrole-2,5-dione (250 mg, 0.65 mmol), prepared as described in U.S. Ser. No. 09/268,887, was dissolved in THF (15 ml) and cooled to −60° C. To this solution was added lithium bis(trimethylsilyl)amide (0.7 mmol, 0.7 ml, 1.0 M in THF), followed by oleyl chloride (Aldrich) (0.300 g, 1.0 mmol) in THF (5 ml). The resulting mixture was stirred at 0° C. for 1 hr. All solvent was evaporated and the crude material was pre-purified by silica gel chromatography. The resulting products were separated using silica gel chromatography using a gradient of ethyl acetate and hexane. This gave 310 mg of 3-(1H-Indol-3-yl)-4-(1-methyl-6-nitro-1H-indol-3-yl)-1-octadec-9-enoyl-pyrrole-2,5-dione. (Yield 70 %)

Example 5

{3-[4-(1-Methyl-6-nitro-1H-indol-3-yl)-2,5-dioxo-2,5-dihydro-1H-pyrrol-3-yl]-indol-1-yl}-phosphonic acid a) A solution of 3-(1H-indol-3-yl)-4-(1-methyl-6-nitro-1H-indol-3-yl)-pyrrole-2,5-dione (210 mg, 0.55 mmol), prepared as described in U.S. Ser. No. 09/268,887, in THF (150 ml) and cooled to −70° C. To this solution was added lithium bis(trimethylsilyl)amide (1.5 mmol, 1.5 ml, 2.5 eq, 1.0 M in THF). To this was added dibenzyl chlorophosphate (CAS: 538-37-4) (500mg, 1.6 mmol) in THF (5 ml). The cooling bath was removed and when the temperature of the solution reached −40° C., the solution was poured in water and extracted into ethyl acetate/hexane (1:4). The organics were washed with water, dried and evaporated. The residue was purified and separated into component products by silica gel chromatography using a gradient of ethyl acetate/hexane. This gave 150 mg of {3-[4-(1-methyl-6-nitro-1H-indol-3-yl)-2,5-dioxo-2,5-dihydro-1H-pyrrol-3-yl]-indol-1-yl}-phosphonic acid dibenzyl ester. (Yield 43 %).

b) A solution of {3-[4-(1-methyl-6-nitro-1H-indol-3-yl)-2,5-dioxo-2,5-dihydro-1H-pyrrol-3-yl]-indol-1-yl}-phosphonic acid dibenzyl ester (50 mg, 0.08 mmol) (from step a) above) in a mixture of THF/ethanol (3 ml/6 ml) was treated with 10% Pd/C (75 mg) and 1,4-cyclohexadiene (0.5 ml) and warmed to 35–40° C. for 2 hr. The reaction was cooled, filtered through celite and evaporated to dryness. Crystals were obtained from THF/hexane to yielding 20 mg of {3-[4-(1-methyl-6-nitro-1H-indol-3-yl)-2,5-dioxo-2,5-dihydro-1H-pyrrol-3-yl]-indol-1-yl}-phosphonic acid. (Yield 55 %)

Example 6

3-(1-Acetyl-1H-indol-3-yl)-4-(1-methyl-6-nitro-1H-indol-3-yl)-pyrrole-2,5-dione

A solution of 3-(1 H-indol-3-yl)-4-(1-methyl-6-nitro-1H-indol-3-yl)-pyrrole-2,5-dione (51 mg, 0.13 mmol), prepared as described in U.S. Ser. No. 09/268,887, in THF (20 ml) and cooled to −70° C. To this solution was added lithium bis(trimethylsilyl)amide (0.5 mmol, 0.5 ml, 3.8 eq, 1.0 M in THF, followed by excess acetyl chloride (0.1 ml). The resulting solution was stirred until the temperature reached −45° C. The reaction was evaporated and purified by silica gel chromatography to give 33 mg of 3-(1-acetyl-1H-indol-3-yl)-4-(1-methyl-6-nitro-1H-indol-3-yl)-pyrrole-2,5-dione. (Yield 65 %).

Example 7

Trifluoro-acetic acid 3-(1-methyl-6-nitro-1H-indol-3-yl)-4-[1-(piperidine-4-carbonyl)-1H-indol-3-yl]-pyrrole-2,5-dione 1.5 equivalents of N-(tert-butoxycarbonyl)-piperidine-4-carboxylic acid (Bachem, Calif.) were added to a solution of 3-(1H-indol-3-yl)-4-(1-methyl-6-nitro-1H-indol-3-yl)-pyrrole-2,5-dione (prepared as described in U.S. Ser. No. 09/268,887 (Compound 1), the relevant portions of which are herein incorporated by reference) in THF. 1.3 equivalents each of diisopropyl carbodiimide and N-Hydroxybenztriazole were added. This solution was stirred at RT for 6.5 hrs. A small amount of Cesium carbonate and 0.5 ml DMF were added. The reaction was stirred for 20 min. The reaction mixture was then diluted with $CH_2Cl_2$ and washed with saturated $NH_4Cl$ and water. The product was purified by flash chromatography. (Yield 92%). The resulting BOC protected amine was dissolved in $CH_2Cl_2$ and treated with trifluoroacetic acid at RT for 1 hr. The solvent was evaporated and the residue was purified by HPLC yielding trifluoro-acetic acid; 3-(1-methyl-6-nitro-1H-indol-3-yl)-4-[1-(piperidine-4-carbonyl)-1H-indol-3-yl]-pyrrole-2,5-dione. (Yield 54%).

Example 8

3-(1-Aminoacetyl-1H-indol-3-yl)-4-(1-methyl-6-nitro-1H-indol-3-yl)-pyrrole-2,5-dione hydrochloride 1.05 equivalents of N-(tert-butoxycarbonyl)glycine (Bachem, Calif.) and 1 equivalent of 3-(1H-Indol-3-yl)-4-(1-methyl-6-nitro-1H-indol-3-yl)-pyrrole-2,5-dione (prepared as above) were dissolved in THF. 1.3 equivalent each of N-hydroxybenzotriazole and diisopropylcarbodiimide were added and the reaction was stirred for 5 hrs. A small amount of Cesium carbonate and DMF were added. The reaction was stirred for 30 min. The reaction mixture was diluted with ethyl acetate and ether, washed with water and dried over sodium sulfate. The resulting 3-[N-butyloxycarbonyl-(1-aminoacetyl-1H-indol-3-yl)]-4-(1-methyl-6-nitro-1H-indol-3-yl)-pyrrole-2,5-dione was purified on a Prep TLC plate. (Yield 53%). The BOC-protected product was dissolved in THF and 12N HCl was added dropwise. The reaction was stirred at RT for 2 hrs. The reaction was concentrated under a stream of $N_2$ and purified by HPLC, to afford 0.026 g 3-(1-aminoacetyl-1H-indol-3-yl)-4-(1-methyl-6-nitro-1H-indol-3-yl)-pyrrole-2,5-dione. (Yield 95%).

Example 9

Acetic acid 3-[4-(1-methyl-6-nitro-1H-indol-3-yl)-2,5-dioxo-2,5-dihydro-1H-pyrrol-3-yl]-indol-1-ylmethyl ester A slurry of 3-(1-hydroxymethyl-1H-indol-3-yl)-4-(1-methyl-6-nitro-1H-indol-3-yl)-pyrrole-2,5-dione (120 mg, 0.288 mmol) (prepared as described in U.S. Ser. No. 09/268,887 (Compound II)) in 3 mL of acetic anhydride (Aldrich) was stirred at room temperature for 19 hours, and at 100° C. for 2.5 hours. The resulting solution was cooled, diluted with water, and extracted with EtOAc. The EtOAc layer was washed with water, brine, dried over magnesium sulfate, and evaporated. The residue was purified by flash chromatography using EtOAc/hexanes to give 77.1 mg of acetic acid 3-[4-(1-methyl-6-nitro-1H-indol-3-yl)-2,5-dioxo-2,5-dihydro-1H-pyrrol-3yl]-indol-1-ylmethyl ester. (Yield 53%).

Example 10

Pentanedioic acid mono-{3-[4-(1-methyl-6-nitro-1H-indol-3-yl)-2,5-dioxo-2,5-dihydro-1H-pyrrol-3-yl]-indol-1-ylmethyl} ester A solution of 3-(1-hydroxymethyl-1H-indol-3-yl)-4-(1-methyl-6-nitro-1H-indol-3-yl)-pyrrole-2,5-dione(103 mg, 0.248 mmol), (prepared as described above in Example 1), glutaryl anhydride (35.1 mg, 0.308 mol) (Aldrich), and triethylamine (0.03 ml, 0.924 mmol) in 5 mL of EtOAc was heated at reflux for 6 hours. The solution was cooled, diluted with EtOAc, washed with 0.5 N HCl, water, brine, dried over magnesium sulfate, and evaporated. The residue was purified by flash chromatography using EtOAc/acetone to give 35 mg of pentanedioic acid mono-{3-[4-(1-methyl-6-nitro-1H-indol-3-yl)-2,5-dioxo-2,5-dihydro-1H-pyrrol-3-yl]-indol-1-ylmethyl} ester. (Yield 27 %).

Example 11

2,3-Dimethoxy-benzoic acid 1-{3-[4-(1-methyl-6-nitro-1H-indol-3-yl)-2,5-dioxo-2,5-dihydro-1H-pyrrol-3-yl]-indol-1-yl}-ethyl ester a) To a suspension of NaH (1.92 gm of a 60% dispersion in oil) in 75 mL of DMF was added indole (4.68 gm, 40 mmol) (Aldrich). The mixture was stirred for 15 minutes at 0° C., and 1-chloroethyl methylether (4 mL) was added dropwise. The resulting mixture was stirred at 0° C. for 1 hour and poured over ice/water, and extracted with toluene. The organic layer was dried over magnesium sulfate, and evaporated. The residue was purified by flash chromatography using EtOAc/hexanes to give 4 gm of 1-[1-methoxyethyl]indole. (Yield 58%).

b) To a solution of 1-(1-methoxyethyl)indole (4 gm, 23 mmol) (prepared as in step a) above) in anhydrous diethyl ether at 0° C. was added oxalyl chloride (4.2 mL, 48 mmol) over 5 minutes. The resulting slurry was stirred at 0° C. for 5 hours, and filtered to afford 1.9 gm of [1-(1-methoxy-ethyl)-1H-indol-3-yl]-oxo-acetyl chloride. (Yield 31%). The material was used without further purification.

c) To a slurry of [1-(1-methoxy-ethyl)-1H-indol-3-yl]-oxo-acetyl chloride (1.9 gm, 7.15 mmol) (from step b) above) and [1-methyl-6-nitro-1H-indol]-3-ethenimidic acid 1-methylethyl ester hydrochloride (2.3 gm, 7.3 mmol) (Compound 15 in Scheme 2 of U.S. Ser. No. 09/268,887) in 75 mL of CH$_2$Cl$_2$ at 0 C., was added triethylamine (3.6 mL, 25.8 mmol) over 3 minutes. The mixture was stirred at 0° C. for 4 hours, and extracted with 0.5 N HCl. The aqueous layer was extracted with CH$_2$Cl$_2$, and the combined CH$_2$Cl$_2$ layers were washed with water, brine, dried over magnesium sulfate, and evaporated. The residue was dissolved in 70 mL of toluene and the resulting solution was cooled to 0 C. p-toluenesulfonic acid hydrate (1.4 gm, 7.36 mmol) was added and the mixture was stirred at 0° C. for 1 hour. The slurry was washed with saturated NaHCO$_3$ and extracted with 2×50 mL of EtOAc. The combined EtOAC layers were dried over magnesium sulfate and evaporated to give 4.1 gm (Yield 100%) of 3-[1-(1-methoxy-ethyl)-1H-indol-3-yl]-4-(1-methyl-6nitro-1H-indol-3-yl)-pyrrole-2,5-dione as a red gummy solid which was used without purification.

d) To a solution of 3-[1 -(1-methoxy-ethyl)-1H-indol-3-yl]-4-(1-methyl-6-nitro-1H-indol-3-yl)-pyrrole-2,5-dione (3.75 gm) (from step c) above) in 100 mL of THF was added 2 N HCl (75 mL). The solution was stirred at room temperature for 3 hours, and poured into EtOAc and brine. The layers were separated, and the aqueous layer was extracted with EtOAc. The combined EtOAc layers were dried over magnesium sulfate, and evaporated. The residue was purified by flash chromatography using EtOAc/hexanes to give 1.1 gm (Yield 33%) of 3-[1-(1-hydroxy-ethyl)-1H-indol-3-yl]-4-(1-methyl-6-nitro-1H-indol-3-yl)-pyrrole-2,5-dione.

e) To a solution of 3-[1-(1-hydroxy-ethyl)-1H-indol-3-yl]-4-(1-methyl-6-nitro-1H-indol-3-yl)-pyrrole-2,5-dione (165.3 mg, 0.678 mmol) (from step d) above), EDC.HCL (284.5 mg, 1.484 mmol), and dimethylaminopyridine (185.5 mg, 1.58 mmol) in 20 mL of CH$_2$Cl$_2$ was added 2,3-dimethoxybenzoic acid (287.4 mg, 0.668 mmol). The solution was stirred at room temperature for 0.5 hour, washed with saturated NaHCO$_3$, brine, dried over magnesium sulfate, and evaporated. The residue was purified by flash chromatography using EtOAc/hexanes to give 203 mg of 2,3-dimethoxy-benzoic acid 1-{3-[4-(1-methyl-6-nitro-1H-indol-3-yl)-2,5-dioxo-2,5-dihydro-1H-pyrrol-3-yl]-indol-1-yl}-ethyl ester. (Yield 50%).

Example 12

3-Diethylaminomethyl-benzoic acid 1-{3-[4-(1-methyl-6-nitro-1H-indol-3-yl)-2,5-dioxo-2,5-dihydro-1H-pyrrol-3-yl]-indol-1-yl}-ethyl ester hydrochloride 3-Diethylaminomethyl-benzoic acid 1-{3-[4-(1-methyl-6-nitro-1H-indol-3-yl)-2,5-dioxo-2,5-dihydro-1H-pyrrol-3-yl]-indol-1-yl}-ethyl ester hydrochloride was prepared according to the procedure of Example 11 e above using 3-diethylaminomethylbenzoic acid (CAS:137605-77-7) as a starting material. (Yield 50 %).

Example 13

Carbonic acid mono-methylpolyethyleneglycol 2000 ester, 3-[4-(1-methyl-6-nitro-1H-indol-3-yl)-2,5-dioxo-2,5-dihydro-1H-pyrrol-3-yl]-indol-1-ylmethylester Monomethylpolyethyleneglycol (average MW=2000)(1 g, 0.5mmol) was treated with excess 20% phosgene in toluene solution at room temperature for 24 hours and evaporated. The resulting chloroformate in dichloromethane was added to a dry ice/acetone cooled mixture of 3-(1-hydroxymethyl-1H-indol-3-yl)-4-(1-methyl-6-nitro-1H-indol-3-yl)-pyrrole-2,5-dione (208 mg, 0.5 mmol) (prepared as described above in Example 1) and 4-dimethylaminopyridine (244 mg, 2mmol) in dichloromethane. The cooling bath was removed and the mixture stirred at room temperature for one hour. The reaction mixture was purified by flash chromatography using methanol/dichloromethane followed by crystallization of the product fractions from THF/ethyl ether to give 0.8 g of carbonic acid mono-methylpolyethyleneglycol 2000 ester, 3-[4-(1-methyl-6-nitro-1H-indol-3-yl)-2,5-dioxo-2,5-dihydro-1H-pyrrol-3-yl]-indol-1-ylmethylester, as an orange solid, mp 46–48. (Yield 65%).

Example 14

Mono-methylpolyethyleneglycol 2000-carbamic acid, 3-[4-(1-methyl-6-nitro-1H-indo-3-yl)-2,5-dioxo-2,5-dihydro-1H-pyrrol-3-yl]indol-1-ylmethyl ester Lithium bis(trimethylsilyl)amide (0.25mL, 0.25 mmol, 1M in THF) was added dropwise to a solution of 3-(1-hydroxymethyl-1H-indol-3-yl)-4-(1-methyl-6-nitro-1 H-indol-3-yl)-pyrrole-2,5-dione (104 mg, 0.25 mmol)

(prepared as described above in Example 1) in THF (5 mL) at 0° C. After 10 minutes bis(p-nitrophenyl)carbonate (84 mg, 0.275 mmol) was added and the solution was stirred at 0° C. for 10 minutes. Methoxy-PEG2000-amine (0.6 g, 0.3 mmol) (Shearwater Polymers, Inc.) was added and the mixture was warmed to ~40° C. to dissolve the solids. The resulting solution was stirred at room temperature for 2 hours and evaporated to remove solvents. The residue was chromatographed on silica gel using methanol/dichloromethane followed by crystallization of the product fractions from THF/ethyl ether to give 0.425 g of mono-methylpolyethyleneglycol 2000-carbamic acid, 3-[4-(1-methyl-6-nitro-1H-indo-3-yl)-2,5-dioxo-2,5-dihydro-1H-pyrrol-3-yl]indol-1-ylmethyl ester, as an orange solid, mp 49–51° C.(Yield 70%)

Example 15

Antiproliferative Activity

The antiproliferative activity of the compounds of the invention is demonstrated below. These effects indicate that the compounds of the present invention are useful in treating cancer, in particular solid tumors such as breast and colon tumors.

MDAMB435 Cell-Based Assay

The epithelial breast carcinoma cell line (MDAMB-435) was purchased from ATCC (American Type Cell Culture Collection) and was grown in culture in medium as recommended by ATCC. For analysis of the effect of various compounds of formula I on the growth of these cells, the cells were plated at a concentration of 1500 cells/well in a 96 well tissue culture plate ("test plate). The day after the cells were plated, the compounds to be analyzed were dissolved in 100% DMSO (dimethyl sulfoxide) to yield at 10 mM stock solution. Each compound was diluted in $H_2O$ to 1 mM and was added to triplicate wells in the first row of a 96 well master plate containing medium to yield a final concentration of 40 $\mu M$. The compounds were then serially diluted in medium in the "master plate". The diluted compound(s) were then transferred to test plates containing cells. A row of vehicle "control cells" received DMSO. The final concentration of DMSO in each well was 0.1%. 5 days post drug addition, the plate was analyzed as described below.

MTT (3-(4-5 methyl thiazole-2-yl)-2,5-diphenyl tetrazolium bromide; thiazolyl blue) was added to each well to yield a final concentration of 1 mg/ml. The plate was then incubated at 37° C. for 2½–3 hours. The MTT-containing medium was then removed and 50 $\mu l$ of 100% ethanol was added to each well to dissolve the formazan. The absorbencies were then read using an automated plate reader (Bio-tek microplate reader). $IC_{50}$ measurements were calculated using the Reed and Munsch equation, see Am. J. Hygiene Vol. 27 pgs. 493–497,1938.

The results of the foregoing in vitro experiments are set forth in Table I below.

Each of the compounds in Table I had an $IC_{50}<0.3$ $\mu M$.

TABLE I

| Example | R | $IC_{50}$ ($\mu M$) | Scheme |
|---|---|---|---|
| 1 | (structure) | 0.02 | III |
| 2 | (structure) PEG$_{2000}$ | 0.04 | III |
| 3b | (structure) | 0.01 | III |
| 12 | (structure) | 0.01 | III/IV |
| 3a | (structure) | 0.02 | III |
| 11 | (structure) | 0.02 | III/IV |
| 9 | (structure) | 0.02 | III |
| 10 | (structure) | 0.02 | III |
| | (structure with S) | 0.01 | III |

TABLE I-continued

[Structure: bis-indolyl maleimide with R group on one indole N and CH₃ on the other, with NO₂ group]

| Example | R | IC$_{50}$ (μM) | Scheme |
|---------|---|---------------|--------|
| 4 | [oleyl ester: CO-O-(CH₂)₇-CH=CH-(CH₂)₇-CH₃] | 0.3 | II |
| 5 | PO$_3$Na$_2$ | 0.2 | I |
| 6 | COCH$_3$ | 0.01 | II |
| 7 | [CO-O-piperidin-4-yl (NH)] | 0.01 | II |
| 8 | CO-O-CH$_2$-NH$_2$ | 0.01 | II |

These compounds are suitable for administration to patients by continuous infusion.

| Item | Ingredients | Mg/Tablet | | | | | |
|------|-------------|-----|-----|-----|-----|-----|-----|
| 1 | Compound A* | 5 | 25 | 100 | 250 | 500 | 750 |
| 2 | Anhydrous Lactose | 103 | 83 | 35 | 19 | 38 | 57 |
| 3 | Croscarmellose Sodium | 6 | 6 | 8 | 16 | 32 | 48 |
| 4 | Povidone K30 | 5 | 5 | 6 | 12 | 24 | 36 |
| 5 | Magnesium Stearate | 1 | 1 | 1 | 3 | 6 | 9 |
| | Total Weight | 120 | 120 | 150 | 300 | 600 | 900 |

*Compound A represents a compound of the invention.

Manufacturing Procedure:
1. Mix items 1, 2 and 3 in a suitable mixer for 15 minutes.
2. Granulate the powder mix from step 1 with 20% Povidone K30 Solution (Item 4).
3. Dry the granulation from step 2 at 50° C.
4. Pass the granulation from step 3 through a suitable milling equipment.
5. Add the Item 5 to the milled granulation step 4 and mix for 3 minutes.
6. Compress the granulation from step 5 on a suitable press.

Example 17

Capsule Formulation

| Item | Ingredients | mg/Capsule | | | | |
|------|-------------|-----|-----|-----|-----|-----|
| 1 | Compound A* | 5 | 25 | 100 | 250 | 500 |
| 2 | Anhydrous Lactose | 159 | 123 | 148 | — | — |
| 3 | Corn Starch | 25 | 35 | 40 | 35 | 70 |
| 4 | Talc | 10 | 15 | 10 | 12 | 24 |
| 5 | Magnesium Stearate | 1 | 2 | 2 | 3 | 6 |
| | Total Fill Weight | 200 | 200 | 300 | 300 | 600 |

*Compound 1 represents a compound of the invention.

Manufacturing Procedure:
1. Mix items 1, 2 and 3 in a suitable mixer for 15 minutes.
2. Add items 4 & 5 and mix for 3 minutes.
3. Fill into a suitable capsule.

Example 18

Injection Solution/Emulsion Preparation

| Item | Ingredient | mg/mL |
|------|-----------|-------|
| 1 | Compound A* | 1 mg |
| 2 | PEG 400 | 10–50 mg |
| 3 | Lecithin | 20–50 mg |
| 4 | Soy Oil | 1–5 mg |
| 5 | Glycerol | 8–12 mg |
| 6 | Water q.s. | 1 mL |

*Compound A represents a compound of the invention.

Manufacturing Procedure:
1. Dissolve item 1 in item 2.
2. Add items 3, 4 and 5 to item 6 and mix until dispersed, then homogenize.
3. Add the solution from step 1 to the mixture from step 2 and homogenize until the dispersion is translucent.
4. Sterile filter through a 0.2 μm filter and fill into vials.

Example 19 injection Solution/Emulsion Preparation

| Item | Ingredient | mg/mL |
|------|-----------|-------|
| 1 | Compound A* | 1 mg |
| 2 | Glycofurol | 10–50 mg |
| 3 | Lecithin | 20–50 mg |
| 4 | Soy Oil | 1–5 mg |
| 5 | Glycerol | 8–12 mg |
| 6 | Water | q.s. 1 mL |

*Compound A represents a compound of the invention.

Manufacturing Procedure:
1. Dissolve item 1 in item 2.
2. Add items 3, 4 and 5 to item 6 and mix until dispersed, then homogenize.
3. Add the solution from step 1 to the mixture from step 2 and homogenize until the dispersion is translucent.
4. Sterile filter through a 0.2 μm filter and fill into vials.

While the invention has been illustrated by reference to specific and preferred embodiments, those skilled in the art will understand that variations and modifications may be made through routine experimentation and practice of the

What is claimed is:

1. A compound having the formula

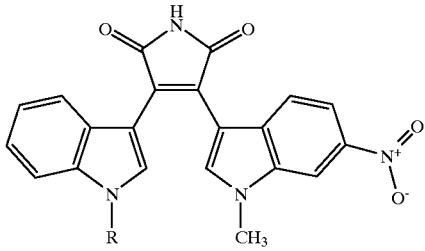

and pharmaceutically active salts of said compounds, wherein:

R is selected from the group consisting of —$PO_3R^1R^2$, —$CHR^3OCOR^4$, —$CHR^3OCO_2R^4$, —$CHR^3OCONHR^4$ and —$COR^4$;

$R^1$ and $R^2$ are selected from the group consisting of H, Na and $NH_4$, and are the same unless either $R^1$ or $R^2$ is H, in which case the other can be different, or alternatively, $R^1$ and $R^2$ together represent Ca;

$R^3$ is selected from the group consisting of H or methyl;

$R^4$ is selected from a group consisting of lower alkyl, which may be optionally substituted by one or more substituents selected from the group consisting of —$CO_2R^5$, —$NR^6R^7$, polyethylene glycol, —$OPO_3R^1R^2$, hydroxy, alkoxy, and aryl, provided that when R is —$COR^4$, $R^4$ is not unsubstituted lower alkyl, alkenyl, which may be optionally substituted by one or more substituents selected from the group consisting of —$CO_2R^5$, —$NR^6R^7$, polyethylene glycol, —$OPO_3R^1R^2$, hydroxy, alkoxy, and aryl, cycloalkyl, which may be optionally substituted by one or more substituents selected from the group consisting of —$CO_2R^5$, —$NR^6R^7$, polyethylene glycol, —$OPO_3R^1R^2$, hydroxy, alkoxy, and aryl, heterocycle, which when including N as a heteroatom the N optionally may be substituted with —$COR^8$, and aryl which optionally may be substituted by one or more substituents selected from the group consisting of —$CO_2R^5$, hydroxy, alkoxy, polyethylene glycol, —$OPO_3R^1R^2$, and alkyl which itself may be substituted with hydroxy, carboxy, and substituted amino;

$R^5$ is selected from the group consisting of H, Na, or lower alkyl;

$R^6$ and $R^7$ are each independently selected from H, lower alkyl, and —$COR^8$, or alternatively, the group —$NR^6R^7$ forms a 5 or 6 membered heterocyclic ring; and $R^8$ is lower alkyl that optionally may be substituted with a polyethylene glycol.

2. A compound having the formula

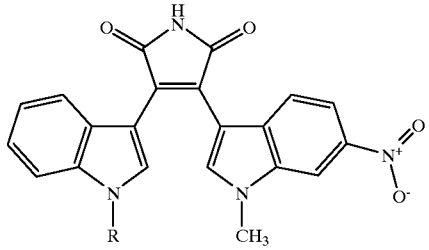

and pharmaceutically active salts of said compounds, wherein:

R is —$CHR^3OCOR^4$;

$R^1$ and $R^2$ are selected from the group consisting of H, Na and $NH_4$, and are the same unless either $R^1$ or $R^2$ is H, in which case the other can be different, or alternatively, $R^1$ and $R^2$ together represent Ca;

$R^3$ is selected from the group consisting of H or methyl;

$R^4$ is selected from a group consisting of lower alkyl, which may be optionally substituted by one or more substituents selected from the group consisting of —$CO_2R^5$, —$NR^6R^7$, polyethylene glycol, —$OPO_3R^1R^2$, hydroxy, alkoxy, and aryl, alkenyl, which may be optionally substituted by one or more substituents selected from the group consisting of —$CO_2R^5$, —$NR^6R^7$, polyethylene glycol, —$OPO_3R^1R^2$, hydroxy, alkoxy, and aryl, cycloalkyl, which may be optionally substituted by one or more substituents selected from the group consisting of —$CO_2R^5$, —$NR^7$, polyethylene glycol, —$OPO_3R^1R^2$, hydroxy, alkoxy, and aryl, heterocycle, which when including N as a heteroatom, the N optionally may be substituted with —$COR^8$, and aryl which optionally may be substituted by one or more substituents selected from the group consisting of —$CO_2R^5$, hydroxy, alkoxy, polyethylene glycol, —$OPO_3R^1R^2$, and alkyl which itself may be substituted with hydroxy, carboxy, and substituted amino;

$R^5$ is selected from the group consisting of H, Na, or lower alkyl;

$R^6$ and $R^7$ are each independently selected from H, lower alkyl, and —COR , or alternatively, the group —$NR^6R^7$ forms a 5 or 6 membered heterocyclic ring; and $R^8$ is lower alkyl that optionally may be substituted with a polyethylene glycol.

3. The compound of claim 2 wherein $R^3$ is H.

4. The compound of claim 3 wherein $R^4$ is lower alkyl.

5. The compound of claim 4 wherein $R^4$ is lower alkyl substituted with polyethylene glycol.

6. The compound of claim 5 wherein the polyethylene glycol has a molecular weight of from about 750 to about 5000 Daltons.

7. The compound of claim 6 wherein the polyethylene glycol has a molecular weight of about 2000.

8. The compound of claim 1 wherein R is —$COR^4$.

9. The compound of claim 8 wherein $R^4$ is heterocycle.

10. A method for treating breast cancer comprising administering to a patient in need thereof a therapeutically effective amount of a compound according to claim 1.

11. The compound of claim 8 wherein $R^4$ is lower alkyl which is substituted with —$NR^6R^7$.

12. The compound of claim 1 wherein the polyethylene glycol has a molecular weight of from about 750 to about 5000 Daltons.

13. The compound of claim 12 wherein the polyethylene glycol has a molecular weight of about 2000 Daltons.

14. A compound selected from the group consisting of:
3-[2-(2-Methoxy-ethoxy)-ethoxy]-propionic acid 3-[4-(1-methyl-6-nitro-1H-indol-3-yl)-2,5-dioxo-2,5-dihydro-1H-pyrrol-3-yl]-indol-1-ylmethyl ester;

O-[2-[[2,5-dihydro-3-[4-(1-methyl-6-nitro-1H-indol-3-yl)-2,5-dioxo-2,5-dihydro-pyrrol-3-yl]-indol-1-yl]methoxycarbonyl]ethyl]-O'-methylpolyethylene glycol 2000;

2,3-Dimethoxy-benzoic acid 3-[4-(1-methyl-6-nitro-1H-indol-3-yl)-2,5-dioxo-2,5-dihydro-1H-pyrrol-3-yl]-indol-1-ylmethyl ester;

3-Diethylaminomethyl-benzoic acid 3-[4-(1-methyl-6-nitro-1H-indol-3-yl)-2,5-dioxo-2,5-dihydro-1H-pyrrol-3-yl]-indol-1-ylmethyl ester hydrochloride;

3-(1H-Indol-3-yl)-4-(1-methyl-6-nitro-1H-indol-3-yl)-1-octadec-9-enoyl-pyrrole-2,5-dione;

{3-[4-(1-Methyl-6-nitro-1H-indol-3-yl)-2,5-dioxo-2,5-dihydro-1H-pyrrol-3yl]-indol-1-yl}-phosphonic acid; and 3-(1-Acetyl-1H-indol-3-yl)-4-(1-methyl-6-nitro-1H-indol-3-yl)-pyrrole-2,5-dione.

15. A compound selected from the group consisting of:

Trifluoro-acetic acid 3-(1-methyl-6-nitro-1H-indol-3-yl)-4-[1-(piperidine-4-carbonyl)-1H-indol-3-yl]-pyrrole-2,5-dione;

3-(1-Aminoacetyl-1H-indol-3-yl)-4-(1-methyl-6-nitro-1H-indol-3-yl)-pyrrole-2,5-dione hydrochloride;

Acetic acid 3-[4-(1-methyl-6-nitro-1H-indol-3-yl)-2,5-dioxo-2,5-dihydro-1H-pyrrol-3-yl]-indol-1-ylmethyl ester;

Pentanedioic acid mono-{3-[4-(1-methyl-6-nitro-1H-indol-3-yl)-2,5-dioxo-2,5-dihydro-1H-pyrrol-3-yl]-indol-1-ylmethyl} ester;

2,3-Dimethoxy-benzoic acid 1-{3-[4-(1-methyl-6-nitro-1H-indol-3-yl)-2,5-dioxo-2,5-dihydro-1H-pyrrol-3-yl]-indol-1-yl}-ethyl ester; and 3-Diethylaminomethyl-benzoic acid 1-{3-[4-(1-methyl-6-nitro-1H-indol-3-yl)-2,5-dioxo-2,5-dihydro-1H-pyrrol-3-yl]-indol-1-yl}-ethyl ester hydrochloride.

16. A pharmaceutical composition comprising a pharmaceutically acceptable carrier or excipient and, as an active ingredient, an effective amount of a compound having the formula

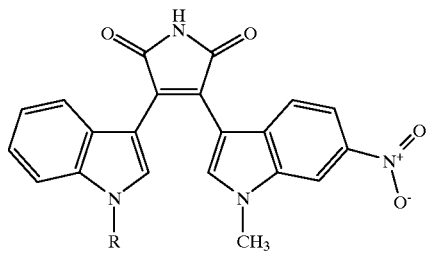

and pharmaceutically active salts of the compound of formula I wherein:

R is selected from the group consisting of $-PO_3R^1R^2$, $-CHR^3OCOR^4$, $-CHR^3OCO_2R^4$, $-CHR^3OCONHR^4$ and $-COR^4$;

$R^1 R^2$ are selected from the group consisting of H, Na and $NH_4$, and are the same unless either $R^1$ or $R^2$ is H, in which case the other can be different, or alternatively, $R^1$ and $R^2$ together represent Ca;

$R^3$ is selected from the group consisting of H or methyl;

$R^4$ is selected from a group consisting of lower alkyl, which may be optionally substituted by one or more substituents selected from the group consisting of $-CO_2R^5$, $-NR^6R^7$, polyethylene glycol, $-OPO_3R^1R^2$, hydroxy, alkoxy, and aryl, provided that when R is $-COR^4$, $R^4$ is not unsubstituted lower alkyl, alkenyl, which may be optionally substituted by one or more substituents selected from the group consisting of $-CO_2R^5$, $-NR6R^7$, polyethylene glycol, $-OPO_3R^1R^2$, hydroxy, alkoxy, and aryl, cycloalkyl, which may be optionally substituted by one or more substituents selected from the group consisting of $-CO_2R^5$, $-NR^6R^7$, polyethylene glycol, $-OPO_3R^1R^2$, hydroxy, alkoxy, and aryl, heterocycle, which when including N as a heteroatom, the N optionally may be substituted with $-COR^8$, and aryl which optionally may be substituted by one or more substituents selected from the group consisting of $-Co_2R^5$, hydroxy, alkoxy, polyethylene glycol, $-OPO_3R^1R^2$, and alkyl which itself may be substituted with hydroxy, carboxy, and substituted amino;

$R^5$ is selected from the group consisting of H, Na, or lower alkyl;

$R^6$ and $R^7$ are each independently selected from H, lower alkyl, and $-COR^8$, or alternatively, the group $-NR^6R^7$ forms a 5 or 6 membered heterocyclic ring; and $R^8$ is lower alkyl that optionally may be substituted with a polyethylene glycol.

17. The pharmaceutical composition of claim 16 which is suitable for parenteral administration.

* * * * *

UNITED STATES PATENT AND TRADEMARK OFFICE
CERTIFICATE OF CORRECTION

PATENT NO. : 6,313,143 B1
DATED : November 6, 2001
INVENTOR(S) : Nader Fotouhi, Emily Aijun Liu, Allen John Lovey, John Guilfoyle Mullin, Jr. and Giuseppe Federico Weber It is certified that error appears in the above-identified patent and that said Letters Patent is hereby corrected as shown below:

Column 22,
Line 36, "-NR R$^7$," should read -- -NR$^6$R$^7$, --.
Line 48, "alkyl, and – COR," should read -- alkyl, and –COR$^8$, --.

Column 24,
Line 30, "-NR6R$^7$," should read -- NR$^6$R$^7$--.
Line 39,"-Co$_2$R$^5$," should read -- -CO$_2$R$^5$, --.

Signed and Sealed this

Twenty-seventh Day of August, 2002

Attest:

JAMES E. ROGAN
Attesting Officer  Director of the United States Patent and Trademark Office